(12) United States Patent
Umebayashi

(10) Patent No.: US 11,850,129 B2
(45) Date of Patent: Dec. 26, 2023

(54) APPARATUS AND METHOD FOR MANUFACTURING ABSORBENT CORE USED IN DISPOSABLE WEARABLE ARTICLE

(71) Applicant: ZUIKO CORPORATION, Osaka (JP)

(72) Inventor: Toyoshi Umebayashi, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 274 days.

(21) Appl. No.: 17/600,583

(22) PCT Filed: Mar. 14, 2020

(86) PCT No.: PCT/JP2020/011312
§ 371 (c)(1),
(2) Date: Sep. 30, 2021

(87) PCT Pub. No.: WO2020/209006
PCT Pub. Date: Oct. 15, 2020

(65) Prior Publication Data
US 2022/0211549 A1    Jul. 7, 2022

(30) Foreign Application Priority Data
Apr. 10, 2019   (JP) ................. 2019-074625

(51) Int. Cl.
*A61F 13/15*    (2006.01)
*D04H 1/736*    (2012.01)

(52) U.S. Cl.
CPC .. *A61F 13/15658* (2013.01); *A61F 13/15764* (2013.01); *D04H 1/736* (2013.01);
(Continued)

(58) Field of Classification Search
CPC .......... A61F 13/15699; A61F 13/15707; A61F 13/15723; A61F 13/565; A61F 13/15658;
(Continued)

(56) References Cited

U.S. PATENT DOCUMENTS 4,764,325 A    8/1988  Angstadt
10,070,996 B2 *  9/2018  Umebayashi ..... A61F 13/15804
(Continued)

FOREIGN PATENT DOCUMENTS

EP    3954350 A1 *  2/2022  ....... A61F 13/15658
JP    2541558 B2    7/1996
(Continued)

OTHER PUBLICATIONS

International Search Report Issued in PCT/JP2020/011312 dated Jun. 16, 2020.

*Primary Examiner* — Jose A Fortuna
(74) *Attorney, Agent, or Firm* — Renner, Otto, Boisselle & Sklar, LLP

(57)    ABSTRACT

A method for manufacturing an absorbent core uses a feed device feeding crushed fiber, a first drum provided with a first area, where the crushed fiber is sucked and stacked, and a second drum provided with a second area, where the crushed fiber is sucked stacked, the second area being smaller than the first area, the method includes a step of forming a thick portion on the second area of the second drum by stacking the fiber fed from the feed device; a step of transferring the thick portion to a predetermined position in the first area; and a step of forming a thin portion on the first area of the first drum by stacking the fiber fed from the feed device around the transferred thick portion with the transferred thick portion placed on the first area.

20 Claims, 2 Drawing Sheets

(52) U.S. Cl.
CPC .............. *A61F 2013/15926* (2013.01); *D10B 2501/00* (2013.01); *D10B 2509/026* (2013.01)

(58) Field of Classification Search
CPC ...... A61F 13/15764; A61F 2013/15926; A61F 13/15642; D04H 1/736; D04H 1/732; B29L 2031/4878; B32B 2555/02; D10B 2501/00; D10B 2509/026
See application file for complete search history.

(56) References Cited

U.S. PATENT DOCUMENTS

| | | | |
|---|---|---|---|
| 10,130,522 B2* | 11/2018 | Umebayashi | A61F 13/15593 |
| 2014/0338822 A1 | 11/2014 | Mukai et al. | |
| 2020/0352793 A1 | 11/2020 | Satou | |
| 2022/0211549 A1* | 7/2022 | Umebayashi | D04H 1/736 |
| 2022/0287886 A1* | 9/2022 | Umebayashi | A61F 13/15658 |
| 2023/0081149 A1* | 3/2023 | Weber | D04H 3/005 |
| 2023/0233382 A1* | 7/2023 | Umebayashi | A61F 13/15747 |
| | | | 156/192 |
| 2023/0241561 A1* | 8/2023 | Marrano | D04H 1/425 |
| | | | 366/163.2 |

FOREIGN PATENT DOCUMENTS

| | | |
|---|---|---|
| JP | 2013-46663 A | 3/2013 |
| WO | WO 2019-097988 A1 | 5/2019 |

* cited by examiner

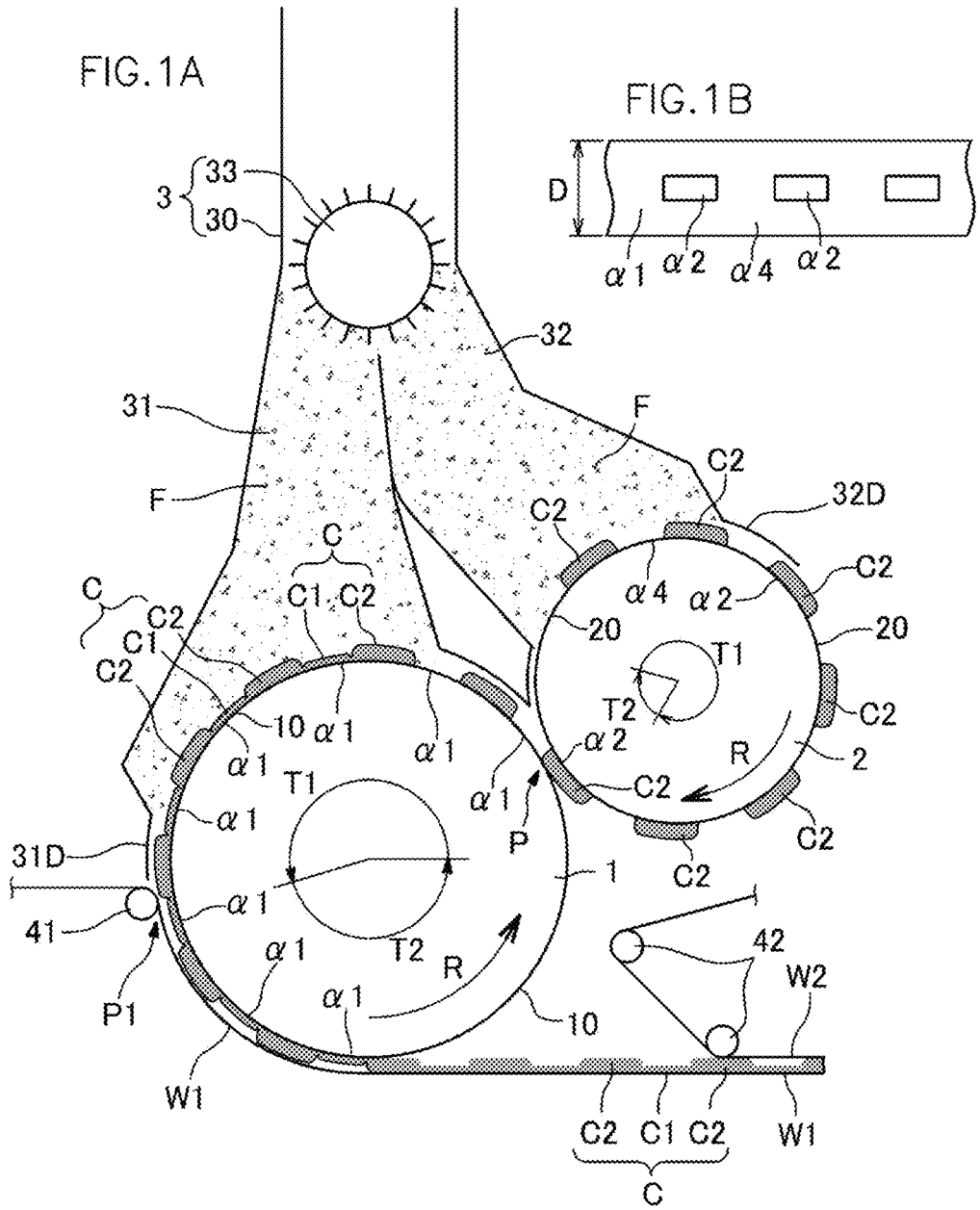

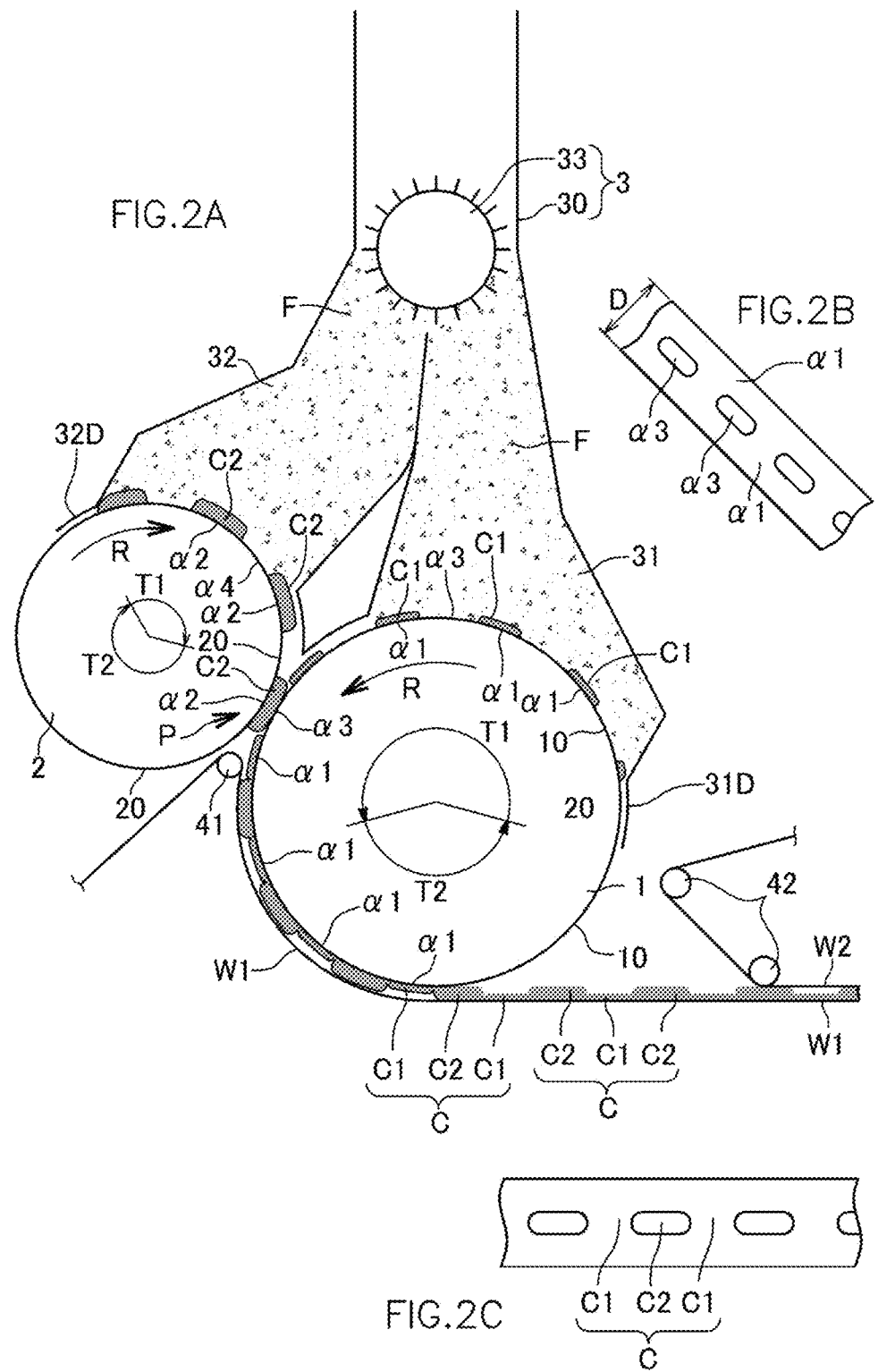

APPARATUS AND METHOD FOR MANUFACTURING ABSORBENT CORE USED IN DISPOSABLE WEARABLE ARTICLE

TECHNICAL FIELD

The present invention relates to an apparatus and a method for manufacturing an absorbent core used in a disposable wearable article.

BACKGROUND ART

For manufacturing an absorbent article such as diaper, there has been a technique in which a partial area in an absorbent core is made have different thickness from the other area in the core. In the technique, one of the two fiber stacking drums forms a first absorbent layer; another of the two fiber stacking drums forms a second absorbent layer, which has a smaller area than the first absorbent layer; and the first and second absorbent layers overlap with each other, thereby producing an absorbent core, which has a partial area thicker than the rest.

SUMMARY OF INVENTION

Since the convention technique overlaps the two layers by simply putting the one on the other, the two layers are likely to be out of alignment during transporting or using the absorbent article.

It is an object of the present invention to provide a method and an apparatus for manufacturing an absorbent core having portions that are different in thickness, the different thickness portions being prevented from out of alignment.

A first method for manufacturing an absorbent core uses a feed device 3, a first drum 1, and a second drum 2,
the feed device 3 feeds crushed fiber F,
the first drum 1 is provided with a first area α1, where the crushed fiber F is sucked and made to cling to an outer circumferential portion 10 of the first drum 1 and stacked, and
the second drum 2 is provided with a second area α2, where the crushed fiber F is sucked and made to cling to an outer circumferential portion 20 of the second drum 2 and stacked, the second area α2 being smaller than the first area α1,
wherein the method comprises:
a step of forming a thick portion C2 on the second area α2 of the second drum 2 by stacking the fiber F fed from the feed device 3;
a step of transferring (placing) the thick portion C2 to a predetermined position in the first area α1; and
a step of forming a thin portion C1 on the first area α1 of the first drum 1 by stacking the fiber F fed from the feed device 3 around the transferred thick portion C2, with the transferred thick portion C2 placed on the first area α1.

With this first method, the thick portion C2 stacked on the second drum 2 is transferred to the first drum 1, and then the thin portion C1 is stacked on the first drum 1. Thus, the thin portion C1 is stacked around the thick portion C2, and the thin portion C1 and the thick portion C2 are unlikely to be out of alignment with each other.

A second method for manufacturing an absorbent core uses a feed device 3, a first drum 1, and a second drum 2,
the feed device 3 feeds crushed fiber F,
the first drum 1 is provided with a first area α1, where the crushed fiber F is sucked and made to cling to an outer circumferential portion 10 of the first drum 1 and stacked, and
the second drum 2 is provided with a second area α2, where the crushed fiber F is sucked and made to cling to an outer circumferential portion 20 of the second drum 2 and stacked, the second area α2 being smaller than the first area α1,
wherein the method comprises:
a step of forming a thick portion C2 on the second area α2 of the second drum 2 by stacking the fiber F fed from the feed device 3;
a step of forming a thin portion C1 on the first drum 1, the thin portion C1 having a grammage lower (a thickness thinner) than a grammage (a thickness) of the thick portion C2 on the first area α1 other than (except) an inhibition area α3, the inhibition area α3 being an area where stacking of the fiber F of the thin portion C1 is inhibited; and
a step of transferring the thick portion C2 from the second drum 2 to the inhibition area α3 of the first drum 1 and fitting the thick portion C2 into the thin portion C1.

With this second method, the thin portion C1 is formed on the first drum 1, and then the thick portion C2 on the second drum 2 is transferred from the second drum 2 to the inhibition area α3 (an area where the thin portion C1 is not formed) of the first drum 1, the thick portion C2 and the thin portion C1 fitting with each other. Thus, the thin portion C1 is positioned around the thick portion C2. Therefore, the thin portion C1 and the thick portion C2 are unlikely to be out of alignment.

An apparatus of the present invention includes:
a feed device 3 that feeds crushed fiber F;
a first drum 1 that forms a thin portion C1 on a first area α1, where the fiber F is sucked and made to cling to an outer circumferential portion 10 of the first drum 1 and stacked;
a second drum 2 that forms a thick portion C2 on a second area α2, where the fiber F is sucked and made to cling to an outer circumferential portion 20 of the second drum 2 and stacked, the second area α2 being smaller than the first area α1;
a first duct portion 31 that guides the fiber F from the feed device 3 to the outer circumferential portion 10 of the first drum 1,
a second duct portion 32 that guides the fiber F from the feed device 3 to the outer circumferential portion 20 of the second drum 2; and
a point P defined between the first duct portion 31 and the second duct portion 32,
the first drum 1 and the second drum 2 making contact with each other, with the thick portion C2 placed between the first drum 1 and the second drum 2 at the point P, and the thick portion C2 stacked on the second area α2 being passed from the second drum 2 to an area in the first drum 1 where the thin portion C1 is not formed.

With this apparatus of the present invention, the thick portion C2 formed on the second drum 2 is transferred to the first drum 1 and placed on an area where the thin portion C1 is not formed. Thus, the thin portion C1 is stacked so as to surround the thick portion C2. Therefore, the thin portion C1 and the thick portion C2 are unlikely to be out of alignment.

BRIEF DESCRIPTION OF DRAWINGS

FIG. 1A is a conceptional side view showing an embodiment 1 of the present apparatus and the present method, FIG. 1B is a developed view showing an area of the drum, and FIG. 1C is a perspective view of the absorbent core.

FIG. 2A is a conceptional side view showing an embodiment 2 of the present apparatus and the present method, FIG. 2B is a developed view showing an area of the drum, and FIG. 2C is a plan view of the absorbent core.

DESCRIPTION OF EMBODIMENTS

In the first method of the present invention, it is preferred that the thick portion C2 on the second drum 2 is placed in the first area α1 of the first drum 1 by being sucked and made to cling to the first area α1 in a state where the fiber F of the thin portion C1 is not yet stacked in the first area α1.

In this case, the thick portion C2 on the second drum 2 is placed on the first area α1 of the first drum 1 and sucked in the first area α1, so the thick portion C2 is more likely to be out of alignment.

In the second method of the present invention, it is preferred that, in the step of forming the thick portion C2 on the second drum 2, the thick portion C2 is formed so as to coincide with a planar shape of the inhibition area α3 of the first drum 1.

In this case, it is possible to transfer the thick portion C2 to the inhibition area α3, with the thick portion C2 being coincided with the inhibition area α3 in shape.

In the second method of the present invention, in the step of forming the thin portion C1 on the first drum 1, the fiber F may not be stacked in the inhibition area α3.

In the methods of the present invention, in the step of forming the thin portion C1, the thin portion C1 may continuously be formed along the outer circumferential portion 10 of the first drum 1 so as to form the absorbent core C, which is continuous.

In this case, the continuous absorbent core C is cut in an individual wearable article unit.

In the methods of the present invention, the absorbent core C is formed such that a surface of the thick portion C2 protrudes more than (higher than) a surface of the thin portion C1.

In the case where the device of the present invention is applied to the first method of the present invention, the second drum 2 makes contact with the first drum 1 at the point P, with the thick portion C2 placed between the first drum 1 and the second drum 2, such that the thick portion C2 stacked on the second drum 2 is passed (transferred) from the second drum 2 to the first drum 1 in a state where the thin portion C1 is not yet stacked on the first drum 1.

On the other hand, in the case where the device of the present invention is applied to the second method of the present invention, the second drum 2 makes contact with the first drum 1 at the point P, with the thick portion C2 placed between the first drum 1 and the second drum 2, such that the thick portion C2 stacked on the second drum 2 is transferred from the second drum 2 to an inhibition area α3 of the first drum 1 in a state where the thin portion C1 is stacked on the first drum 1 in the first area α1 other than (except) the inhibition area α3, where stacking of the fiber F of the thin portion C1 is inhibited and the fiber F of the thin portion C1 is not stacked.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

EMBODIMENTS

Embodiments of the present invention will now be described with reference to the drawings.

An absorbent core manufactured by the device of the present invention is used as a core for such as disposable underwear, diapers, and incontinence pads. The core may be in hourglass shape in planar view.

FIG. 1 shows an embodiment 1.

As shown in FIG. 1, a manufacturing device includes a feed device 3, a first drum 1, and a second drum 2.

The feed device 3 includes a cylindrical case 30 and a defibrating machine 33. The defibrating machine 33 defibrates (comminutes) pulp fed from the upstream to produce fluff pulp (fiber). The fluff pulp filled in the case 30 passes through a first duct portion 31 and a second duct portion 32, and is stacked on an outer circumferential portion 10 of the first drum 1 and an outer circumferential portion 20 of the second drum 2 due to negative pressure from respective suction chambers (not shown) of the first and second drums 1, 2. The defibration and stacking described above are well-known technique in the art, and they are disclosed in JP2009-112438 A, for example.

Note that high molecular compound particles (super absorbent polymer particles), as it is called SAP, having high absorbing capacity may be added as a construction material for the absorbent core.

The first and second drums 1, 2 are in an approximately cylindrical shape, and are formed by plural segments (not shown) as in the well-known art. The first drum 1 and the second drum 2 are provided with the first duct portion 31 and the second duct portion 32, respectively. These drums 1, 2 continuously rotate in the circumferential direction R, and suck the fiber F fed from the feed device 3 from the outer circumferential portions 10, 20 of these drums 1, 2 toward the respective inside suction chambers (not shown). Thus, the fiber F is continuously clung to and stacked on a predetermined first area α1 in the outer circumferential portion 10 and a predetermined second area α2 in the outer circumferential portion 20.

The suction chambers are provided to the respective drums 1, 2 so as to correspond to a predetermined suction section T1 along the circumferential direction R. Each suction chamber is connected to a negative pressure source (not shown) so that the chamber is in negative pressure. The suction chambers are positioned close to the inside of the outer circumferential portion 10, 20 of the respective drums 1, 2. Thus, the fiber F is clung to and stacked on the drums 1, 2 during the suction section T1.

On the other hand, each drum 1, 2 is provided with a non-suction section T2, in which the outer circumferential portion 10, 20 of the drums does not pass by the suction chamber.

In the present embodiment, the first area α1 of the first drum 1 is continuously provided in the circumferential direction R of the first drum 1, whereas the second area α2 of the second drum 2 is intermittently provided at regular intervals in the circumferential direction R of the second drum 2. In general, each area α1, α2 is formed in a concave drum surface. The concave surface, a basic construction and a detailed construction of a drum are well known, and they are disclosed in JP 2,541,558 B2, JP 4,312,112 B2, and JP 3,153,060 B2, for example.

As shown in FIG. 1B, the second area α2 is provided so as to be embraced in the first area α1. For example, in the present embodiment, the intermittently-provided second area α2 is smaller in the circumferential direction R and the width direction D than the continuously-provided first area α1, and is provided so as to be embraced. In the second drum 2 of FIG. 1A, an area in the outer circumferential portion 20 other than the second area α2 is an inhibition area α4, where the stacking of the fiber F is inhibited.

Note that the first area α1 may be in hourglass shape in planar developed view and may be non-continuous.

In the first area α1 of FIG. 1B, a thin portion C1 of FIG. 1C is formed. In the second area α2 of FIG. 1B, a thick portion C2 of FIG. 1C is formed.

The first and second duct portions 31, 32 of FIG. 1A are connected to the case 30 of the feed device 3, and guide the fiber F from the feed device 3 to the outer circumferential portion 10 of the first drum 1 and the outer circumferential portion 20 of the second drum 20, respectively. A part of the outer circumferential portion 10, 20 of each of the first and second drums 1, 2 faces the end of the respective first and second duct portions 31, 32.

At least a part of the suction section T1 of each drum 10, 20 faces an end opening of the respective duct portions 31, 32. Note that a dome 31D, 32D extending along a drum may be formed at the end of each duct portion.

The thick portion C2 is more bulky and thicker than the thin portion C1. Such thickness deference between the thin portion C1 and the thick portion C2 is gained by differentiating negative pressure amount in the chambers, or differentiating the suction periods, for example.

The first drum 1 and the second drum 2 contact with each other at a hand-over point P via the thick portion C2 therebetween. At the point P, the first drum 1 is set in the suction section T1, whereas the second drum 2 is set in the non-suction section T2.

Note that the first drum 1 and the second drum 2 may be so close to each other that the second drum 2 can pass the thick portion C2 to the first drum 1 without contacting with each other via the thick portion C2.

At the downstream of the first drum 1, a first conveying portion 41 is provided. The first conveying portion 41 conveys a first web W1 (a carrier web) for conveying the absorbent core C formed by the thin portion C1 and the thick portion C2. At the further downstream of the first conveying portion 41, a second conveying portion 42 is provided. The second conveying portion 42 conveys a second web W2 that is used for sandwiching the absorbent core C in between the first web W1 and the second web W2. Note that the first conveying portion 41 conveys the first web W1 along the first drum 1 so as to sandwich the absorbent core C in between the first web W1 and the first drum 1.

Each conveying portion 41, 42 may include guide rollers, unwinding rollers for web, and anvil rolls that convey and cut the absorbent core C sandwiched in between a pair of webs. Note that a web may have water absorbency and water permeability.

The hand-over point P described above is provided between the first duct portion 31 and the second duct portion 32. At the point P, the first drum 1 and the second drum 2 contact with each other via the thick portion C2 therebetween, and the thick portion C2 stacked on the second area α2 is handed over from the second drum 2 to an area in the first drum 1, wherein the thin portion C1 is not formed in the area.

Next, a method for manufacturing the absorbent core C will be described.

First, when the second drum 2 faces the second duct portion 32 in the suction section T1, the fiber F produced by the feed device 3 is clung to and stacked on the second area α2 to form the thick portion C2. The thick portion C2 is conveyed to the hand-over point P while being sucked on the outer circumferential portion 20 of the second drum 2 at regular intervals.

At the hand-over point P, the thick portion C2 is transferred from the second drum 2 to the first area α1 of the first drum 1. That is, at the point P, the second drum 2 is set in the non-suction section T2, whereas the first drum 1 is set in the suction section T1.

Thus, the thick portion C2 on the second drum 2 is placed on the first area α1 of the first drum 1.

Note that, in the present embodiment, the thick portion C2 is sucked and placed on (transferred to) the first area α1 in a state where the fiber F is not stacked on the first area α1.

A part of the first drum 1, having received the thick portion C2, rotates in the circumferential direction R and faces the first duct portion 31. There the fiber F produced by the feed device 3 is clung to and stacked on the first area α1, thereby producing the continuous thin portion C1 around the thick portion C2. At this stacking, the fiber F may be slightly stacked on the thick portion C2 in the first area α1.

Note that, in the present embodiment, the absorbent core C, in which the thin portion C1 is continuous along the outer circumferential portion 10 of the first drum 1, is formed in the step of forming the thin portion C1.

As a result, the absorbent core C shown in FIG. 1C is formed on the outer circumferential portion 10 of the first drum 1. The formed absorbent core C passes by the dome 31D of the first duct portion 31, and then transferred to the first web W1 guided by the first conveying portion 41 in the non-suction section, and conveyed.

Thereafter, the absorbent core C is sandwiched in between the first web W1 and the second web W2 conveyed by the second conveying portion 42. The sandwiched absorbent core C is cut in an individual wearable article unit.

Note that, as shown in FIG. 1C, the absorbent core C is formed so that the surface of the thick portion C2 protrudes more than the surface of the thin portion C1.

FIG. 2 shows an embodiment 2.

The embodiment 2 will be mainly described for different part from the embodiment 1.

In the present embodiment, an inhibition area α3 is provided in the first drum 1 in addition to the first area α1. In the inhibition area α3, the stacking of the fiber F is inhibited (prevented). For weakening negative pressure suction, the mesh porosity in the outer circumferential portion 10 in the inhibition area α3 may be set to be small. The first drum 1 and the second drum 2 contact with each other at the hand-over point P as follows.

The both drums contact at the point P so that the thick portion C2 stacked on the second drum 2 is passed (handed over) from the second drum 2 to the inhibition area α3 of the first drum 1. The hand-over is performed in a state where the fiber F is clung to and stacked on the first area α1, except the inhibition area α3, of the first drum 1 while the fiber F is not stacked on the inhibition area α3, where stacking of the fiber F is inhibited.

Next, a method for manufacturing an absorbent core C will be described.

First, the thin portion C1 is formed on the first drum 1 in an area other than the inhibition area α3, where stacking of the fiber F is inhibited. The thin portion C1 has a smaller grammage (thinner thickness) than the thick portion C2. At the forming the thin portion C1, the fiber F may not be stacked on the inhibition area α3.

On the other hand, the thick portion C2 is formed on the second drum 2 by stacking the fiber F fed from the feed device 3 on the second area α2. The thick portion C2 is formed on the second drum 2 so as to coincide with the inhibition area α3 of the first drum 1 in planar shape.

Thereafter, at the hand-over point P, the thick portion C2 on the second drum 2 is transferred to the inhibition area α3 of the first drum 1, and the thick portion C2 fits into the thin portion C1. As a result, the continuous absorbent core C of FIG. 2C is produced, being sandwiched in between a pair of the webs W1, W2 as similar to the aforementioned embodiment 1.

Although the preferred embodiments have been described above with reference to the drawings, a person skilled in the art would easily arrive at various changes and modifications within an obvious range through this specification.

For example, each duct portion 31, 32 is connected to different defibrating machines.

Also, the absorbent core C is formed on the drum in an intermittent manner in the circumferential direction R.

Therefore, such changes and modifications are interpreted to be within the scope of the present invention determined from claims.

INDUSTRIAL APPLICABILITY

The present invention is applicable to manufacturing an absorbent core used in a disposable wearable article.

REFERENCE SIGNS LIST

1: First drum
10: Outer circumferential portion
2: Second drum
20: Outer circumferential portion
3: Feed device
31: First duct portion
32: Second duct portion
31D, 32D: Dome
41: First transferring portion
42: Second transferring portion
C: Absorbent core
C1: Thin portion
C2: Thick portion
D: Width direction
F: Fiber
R: Circumferential direction
T1: Suction section
T2: Non-suction section
α1: First area
α2: Second area
α3: Inhibition area

The invention claimed is:

1. A method for manufacturing an absorbent core of a disposable wearable article,
wherein the method uses a feed device, a first drum, and a second drum,
the feed device feeds crushed fiber,
the first drum is provided with a first area, where the crushed fiber is sucked and made to cling to an outer circumferential portion of the first drum and stacked, and
the second drum is provided with a second area, where the crushed fiber is sucked and made to cling to an outer circumferential portion of the second drum and stacked, the second area being smaller than the first area,
wherein the method comprises:
a step of forming a thick portion on the second area of the second drum by stacking the fiber fed from the feed device;
a step of transferring the thick portion to a predetermined position in the first area; and
a step of forming a thin portion on the first area of the first drum by stacking the fiber fed from the feed device around the transferred thick portion with the transferred thick portion placed on the first area, resulting in the absorbent core formed of the crushed fiber.

2. The manufacturing method according to claim 1, wherein the thick portion on the second drum is placed on the first area of the first drum by being sucked and made to cling to the first area in a state where the fiber of the thin portion is not stacked on the first area.

3. The manufacturing method according to claim 2, wherein, in the step of forming the thin portion, the thin portion is continuously formed along the outer circumferential portion of the first drum so as to form the absorbent core, which is continuous.

4. The manufacturing method according to claim 2, wherein the absorbent core is formed such that a surface of the thick portion protrudes more than a surface of the thin portion.

5. The manufacturing method according to claim 1, wherein, in the step of forming the thin portion, the thin portion is continuously formed along the outer circumferential portion of the first drum so as to form the absorbent core, which is continuous.

6. The manufacturing method according to claim 5, wherein the absorbent core is formed such that a surface of the thick portion protrudes more than a surface of the thin portion.

7. The manufacturing method according to claim 1, wherein the absorbent core is formed such that a surface of the thick portion protrudes more than a surface of the thin portion.

8. A method for manufacturing an absorbent core of a disposable wearable article,
wherein the method uses a feed device, a first drum, and a second drum,
the feed device feeds crushed fiber,
the first drum is provided with a first area, where the crushed fiber is sucked and made to cling to an outer circumferential portion of the first drum and stacked, and
the second drum is provided with a second area, where the crushed fiber is sucked and made to cling to an outer circumferential portion of the second drum and stacked, the second area being smaller than the first area, wherein the method comprises:

a step of forming a thick portion on the second area of the second drum by stacking the fiber fed from the feed device;

a step of forming a thin portion on the first drum, the thin portion having a grammage lower than a grammage of the thick portion and being formed on the first area except an inhibition area, the inhibition area being an area where stacking of the fiber of the thin portion is inhibited; and a step of transferring the thick portion from the second drum to the inhibition area of the first drum and fitting the thick portion into the thin portion, resulting in the absorbent core formed of the crushed fiber.

9. The manufacturing method according to claim 8, wherein, in the step of forming the thick portion on the second drum, the thick portion is formed so as to coincide with a planar shape of the inhibition area of the first drum.

10. The manufacturing method according to claim 9, wherein, in the step of forming the thin portion on the first drum, the fiber is not stacked on the inhibition area.

11. The manufacturing method according to claim 9, wherein, in the step of forming the thin portion, the thin portion is continuously formed along the outer circumferential portion of the first drum so as to form the absorbent core, which is continuous.

12. The manufacturing method according to claim 9, wherein the absorbent core is formed such that a surface of the thick portion protrudes more than a surface of the thin portion.

13. The manufacturing method according to claim 8, wherein, in the step of forming the thin portion on the first drum, the fiber is not stacked on the inhibition area.

14. The manufacturing method according to claim 13, wherein, in the step of forming the thin portion, the thin portion is continuously formed along the outer circumferential portion of the first drum so as to form the absorbent core, which is continuous.

15. The manufacturing method according to claim 13, wherein the absorbent core is formed such that a surface of the thick portion protrudes more than a surface of the thin portion.

16. The manufacturing method according to claim 8, wherein, in the step of forming the thin portion, the thin portion is continuously formed along the outer circumferential portion of the first drum so as to form the absorbent core, which is continuous.

17. The manufacturing method according to claim 8, wherein the absorbent core is formed such that a surface of the thick portion protrudes more than a surface of the thin portion.

18. An apparatus for manufacturing an absorbent core of a disposable wearable article, comprising:

a feed device that feeds crushed fiber;

a first drum that forms a thin portion on a first area, where the fiber is sucked and made to cling to an outer circumferential portion of the first drum and stacked;

a second drum that forms a thick portion on a second area, where the fiber is sucked and made to cling to an outer circumferential portion of the second drum and stacked, the second area being smaller than the first area;

a first duct portion that guides the fiber from the feed device to the outer circumferential portion of the first drum;

a second duct portion that guides the fiber from the feed device to the outer circumferential portion of the second drum; and a point defined between the first duct portion and the second duct portion, the first drum and the second drum making contact with each other, with the thick portion placed between the first drum and the second drum at the point, and the thick portion stacked on the second area being passed from the second drum to an area in the first drum, where the thin portion is not formed, resulting in the absorbent core formed of the crushed fiber.

19. The manufacturing apparatus according to claim 18, wherein the second drum makes contact with the first drum at the point, with the thick portion placed between the first drum and the second drum, such that the thick portion stacked on the second drum is passed from the second drum to the first drum in a state where the thin portion is not stacked on the first drum.

20. The manufacturing apparatus according to claim 18, wherein the second drum makes contact with the first drum at the point, with the thick portion placed between the first drum and the second drum, such that the thick portion stacked on the second drum is transferred from the second drum to an inhibition area of the first drum in a state where the thin portion is stacked on the first drum on the first area except the inhibition area, where stacking of the fiber of the thin portion is inhibited and the fiber of the thin portion is not stacked.

* * * * *